United States Patent
Lu

(10) Patent No.: US 11,660,217 B2
(45) Date of Patent: May 30, 2023

(54) STENT DELIVERY COMPONENT, STENT DELIVERY SYSTEM AND STENT SYSTEM

(71) Applicant: ACCUMEDICAL BEIJING LTD., Beijing (CN)

(72) Inventor: Yiran Lu, Beijing (CN)

(73) Assignee: ACCUMEDICAL BEIJING LTD., Beijing (CN)

( * ) Notice: Subject to any disclaimer, the term of this patent is extended or adjusted under 35 U.S.C. 154(b) by 0 days.

(21) Appl. No.: 17/331,118

(22) Filed: May 26, 2021

(65) Prior Publication Data

US 2022/0079788 A1  Mar. 17, 2022

(30) Foreign Application Priority Data

Sep. 14, 2020  (CN) .......................... 202010963614.5

(51) Int. Cl.
*A61F 2/95* (2013.01)

(52) U.S. Cl.
CPC ..... *A61F 2/9522* (2020.05); *A61F 2002/9511* (2013.01)

(58) Field of Classification Search
CPC .......... A61F 2/2436; A61F 2/243; A61F 2/97; A61F 2/2418; A61F 2/9522; A61F 2002/9511; A61F 2/966; A61F 2002/9528; A61F 2002/9665; A61F 2/90; A61B 17/29

See application file for complete search history.

(56) References Cited

U.S. PATENT DOCUMENTS

| | | | | |
|---|---|---|---|---|
| 2006/0089627 | A1* | 4/2006 | Burnett | A61B 17/12099 606/1 |
| 2013/0158524 | A1* | 6/2013 | Fargahi | A61F 2/97 606/1 |
| 2017/0258584 | A1* | 9/2017 | Chang | A61F 2/2436 |
| 2017/0290691 | A1 | 10/2017 | Toner et al. | |
| 2018/0206990 | A1* | 7/2018 | Marchand | A61F 2/2436 |

FOREIGN PATENT DOCUMENTS

| | | |
|---|---|---|
| CN | 107835676 A | 3/2018 |
| CN | 108882979 A | 11/2018 |
| CN | 110393616 A | 11/2019 |
| CN | 111904677 A | 11/2020 |

OTHER PUBLICATIONS

Office Action dated Feb. 22, 2021 received in corresponding Chinese priority application No. CN202010963614.5, 11 pages.

* cited by examiner

*Primary Examiner* — Timothy J Neal
*Assistant Examiner* — Andrew P. Restaino
(74) *Attorney, Agent, or Firm* — Morrison & Foerster LLP

(57) ABSTRACT

The present disclosure relates to a stent delivery component, a stent delivery system and a stent system. In particular, a stent delivery component including a base and at least two clamping wings which are rotatably connected with the base, respectively, is provided. In one aspect, the stent delivery component can effectively enclose the stent to complete delivery. In another aspect, the stent delivery component is kept in line contact with an inner wall of a delivery catheter to reduce the contact area, thereby reducing the frictional resistance and being beneficial to reduce the operation difficulty and increasing the delivery efficiency.

21 Claims, 9 Drawing Sheets

STENT DELIVERY COMPONENT, STENT DELIVERY SYSTEM AND STENT SYSTEM

CROSS REFERENCE TO RELATED APPLICATIONS

This application claims priority to Chinese Patent Application No.: 202010963614.5, filed Sep. 14, 2020, which is hereby incorporated by reference in its entirety.

TECHNICAL FIELD

The present disclosure relates to the field of interventional therapy, and particularly relates to a stent delivery component, a stent delivery system and a stent system.

BACKGROUND ART

Vascular stents (or "stents" for short) may be implanted into blood vessels through cardiovascular interventional surgery, and are used to treat various cardiovascular diseases.

In an example, the vascular stent can be used to treat hemangiomata (i.e., used as a blood flow diverter). Hemangioma is a manifestation of localized or diffuse expansion or swelling of the blood vessel wall due to the lesion or injury of the blood vessel wall, with swelling and pulsatile masses as the main manifestations. Hemangioma can occur in any part of an arterial system and a venous system, including cardiovascular, cerebrovascular and peripheral vascular aneurysms. The wall of aneurysm is thin and fragile, so it is easy to rupture. After the vascular stent is implanted into a parent artery, on one hand, the vascular stent can interfere with the blood flow entering a tumor from the parent artery by means of fine meshes, so that blood in the tumor is choked up to form thrombus, promoting the complete blocking of the aneurysm; and on the other hand, the vascular stent can be used for vascular endothelial cells to climb; and after the vascular stent is covered by the vascular endothelial cells, a permanent biological seal can be formed at the neck of the aneurysm, so that the parent artery is restored to be a normal blood vessel.

In another example, the vascular stent can be used to treat vascular lumen blockage. The vascular stent is sent into stenosis of the blood vessel and is expanded, so that the narrowed blood vessel can be restored to be normal, thereby keeping the blood flow unblocked.

Furthermore, the vascular stent can also be used to reduce the elastic recoil after the angioplasty, block torn pieces of endangium, reduce an occurrence rate of acute occlusion during the angioplasty, and reduce the occurrence rate of restenosis.

When the vascular stent is sent into the blood vessel, there are some problems. For example, in a case where a release position of the stent is wrong or the release position needs to be adjusted, the retrieval operation of the stent is very inconvenient. For another example, in a catheter delivery process, relevant personnel usually feel that the delivery operation is laborious and difficult, and the inconvenience in operation reduces the delivery efficiency of the stent.

Therefore, it is necessary to propose a novel technical solution for stent delivery.

SUMMARY OF THE INVENTION

Technical problems to be solved by the present disclosure are as follows: on one hand, the stent is difficult to retrieve, resulting in difficulty in timely adjustment of a release position of the stent in actual operation; and on the other hand, the operation in the delivery process of the stent is laborious and difficult, thus decreasing the delivery efficiency of the stent.

To solve the above technical problems, the inventor found through professional research that one of main reasons for the laborious and difficult operation in stent delivery is that vascular stents are fine instruments, and aneurysm surgery, especially cerebral aneurysm surgery, is one of the top ten difficult operations, which requires extremely high requirement on the operation of doctors. The slight resistance between a delivery component and a catheter is conveyed to hands of doctors through a pushing guide wire, which becomes a great obstacle in the operation. Therefore, the compliance for delivery of the stent in the surgical operation is related to a success rate of the surgery. In order to improve the operation compliance, the inventor performed the profound and meticulous research and further found that a contact surface between a pushing component and a catheter is large, resulting in large frictional force between the pushing component and the catheter, which becomes a main resistance in the stent delivery.

The present disclosure provides the following technical solution:

In a first aspect of the present disclosure, a stent delivery component is provided, which includes a base and at least two clamping wings; the at least two clamping wings are rotatably connected with the base, respectively.

In one embodiment, the at least two clamping wings jointly form an enclosing section of a prismatic shape when being in a first position state, and the enclosing section has an internal space for enclosing at least part of the stent; and the at least two clamping wings are separated from each other to make the enclosing section expanded when rotated from the first position state to a second position state.

Optionally, the rotatable connection is any one or a combination of hinge connection, bearing connection, pin shaft connection and flexible bending connection. Optionally, the stent delivery component is manufactured integrally, and the rotatable connection is the flexible bending connection.

Optionally, the enclosing section has a regular prism shape; and optionally, the enclosing section has any one of a regular quadrangular prism shape, regular pentagonal prism shape and regular hexagonal prism shape. Optionally, the enclosing section has the regular quadrangular prism shape.

The number of the clamping wings is two. The two clamping wings are concave plate structures. Optionally, the internal space of the enclosing section is in a cylindrical or prismatic shape. Optionally, the internal space of the enclosing section is in a prismatic space, and the prismatic space corresponds to the prismatic shape. Optionally, the base is a tubular structure.

Optionally, the stent delivery component includes a polymer material and/or metal material. Optionally, the polymer material is selected from a nylon material, a PTEE material, a Pebax material, a TPU material, a PET material, a PE material, a PVC material, a PC material, a POM material, an organic silicon resin material, an ABS material, a PEEK material and a PU material. Optionally, the metal material is selected from titanium, nickel-titanium alloy, stainless steel, platinum-tungsten alloy, platinum, platinum-iridium alloy and cobalt-chromium alloy.

Optionally, a length of each clamping wing satisfies the formula (1):

$$L \geq \left| \frac{D}{2\sin\theta} \right| \qquad \text{Formula (1)}$$

In the formula (1), D represents an outer diameter of the stent, and $\theta$ represents a rotating angle of the clamping wing relative to the first position state; Optionally, the length L of each clamping wing also satisfies the formula (2):

$$L \leq 0.7 L_0 \qquad \text{Formula (2)}$$

In the formula (2), $L_0$ represents the length of the stent. Optionally, a first hollowing structure is arranged at the junction between two adjacent clamping wings and the base; optionally, the first hollowing structure is a circular hole or a square hole; optionally, a second hollowing structure is arranged at an adjoint of distal ends of the two adjacent clamping wings; and optionally, the second hollowing structure is in a fan shape, an arc shape or a square shape.

In a second aspect of the present disclosure, a stent delivery system is provided, which includes delivery catheters, delivery guide wires and the stent delivery component in any implementation of the first aspect of the present disclosure.

In one embodiment, the base of the stent delivery component is connected fixedly with a distal end of the delivery guide wire; and at least part of the delivery guide wire and the stent delivery component are accommodated in the delivery catheter.

Optionally, the stent delivery system also includes a beaded component; The beaded component includes at least one expanding section; the proximal end of the beaded component is connected fixedly with the distal end of the delivery guide wire or the base of the stent delivery component.

In a third aspect of the present disclosure, a stent system is provided, which includes a stent and the stent delivery system in any implementation of the second aspect of the present disclosure.

In one embodiment, the stent is at least partially accommodated in the internal space of the stent delivery component.

The stent is accommodated in the delivery catheter.

Optionally, the beaded component is at least partially accommodated in the stent; and optionally, the stent is a cardiovascular self-expanding stent, a periphery self-expanding stent or a cerebrovascular self-expanding stent.

The present invention has the beneficial effects:

In the stent delivery component, the stent delivery system and the stent system provided by embodiments of the present disclosure, at least two clamping wings jointly form the enclosing section of the prismatic shape when located in the first position state, and the enclosing section has the internal space for enclosing at least part of the stent, so that on one hand, the stent can be enclosed effectively so as to complete delivery; and on the other hand, the stent delivery component is kept in line contact with an inner wall of the delivery catheter, and the contact area is reduced, thereby reducing the frictional resistance, reducing the operation difficulty and increasing the delivery efficiency.

BRIEF DESCRIPTION OF DRAWINGS

To illustrate technical solutions of embodiments of the present disclosure more clearly, drawings required in the description of the embodiments of the present disclosure are described simply below. Drawings described herein are used to provide further understandings of the present disclosure, which constitutes a part of the present disclosure, wherein schematic embodiments of the present disclosure and illustrations thereof serve to explain the present disclosure and do not constitute an improper limitation to the present disclosure.

Figure 1:
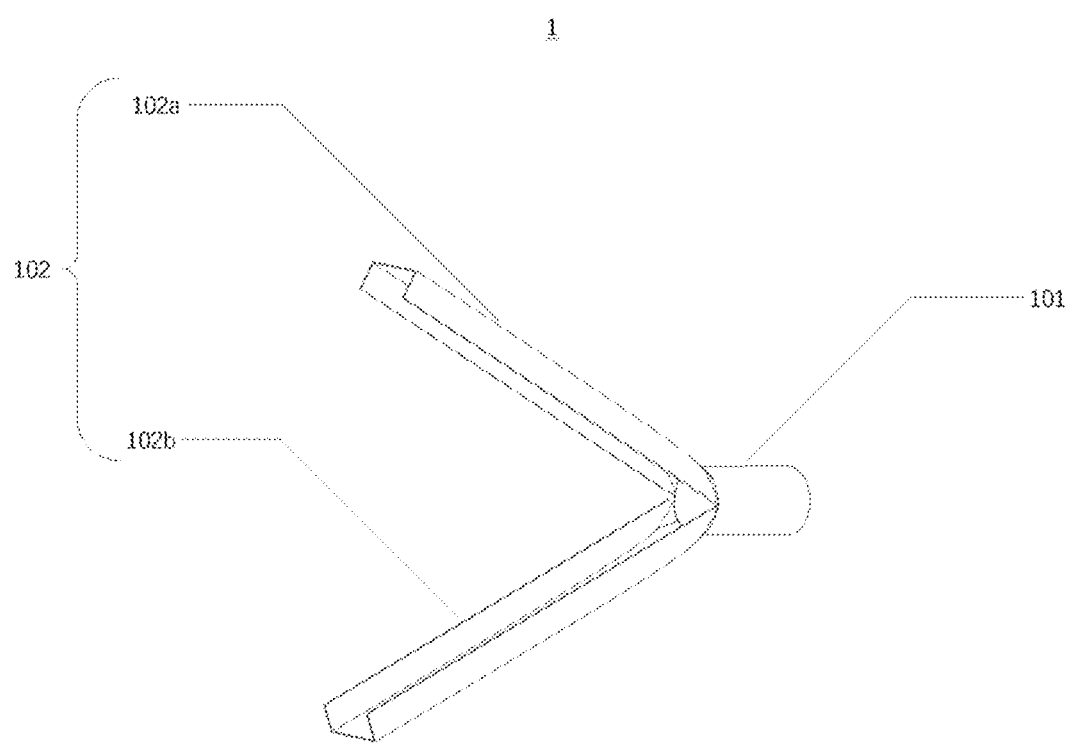
FIG. 1 is a structural schematic diagram of a stent delivery component at a first viewing angle according to an embodiment of the present disclosure.

Numeral references in the drawings: 1—stent delivery component; 101—base; 102—clamping wing; 102a—first clamping wing; 102b—second clamping wing; 102c—third clamping wing; 103—pin shaft; 104—first hollowing structure; 105a-a first portion of a second hollowing structure; 105b-a second portion of the second hollowing structure; 2—stent; 3—delivery guide wire; 4—delivery catheter; 5—beaded component; 501a—first expanding section; 501b—second expanding section; 501c—third expanding section.

DETAILED DESCRIPTION OF THE DISCLOSURE

The present disclosure is further described in detail below in conjunction with the drawings and embodiments. It should be understood that the specific embodiments described herein are merely used to explain relevant invention rather than limiting the invention. Furthermore, it should also be noted that for convenience in description, only parts related to relevant invention are shown in the drawings.

In the description of the present invention, it should be noted that the terms "upper", "lower," "inner", "outer" and the like indicating the orientation or positional relationship are only used for convenience in describing the present invention and simplifying the description, rather than indicating or implying that specified apparatuses or elements must have a specific orientation and be constructed and operated in a specific orientation. Therefore, the terms cannot be understood as limitations to the present invention. Additionally, terms "first", "second" and "third" are only for the purpose of description, and cannot be understood as indicating or implying relative importance.

In the description of the present invention, it should be noted that unless otherwise clearly defined and limited, the terms "installed", "connected" and "connection" should be understood in a broad sense, for example, it can be a fixed connection, a detachable connection, or an integral connection; it can be a mechanical connection or an electrical connection; and it can be a direct connection or an indirect connection through an intermediate medium. For those ordinary skilled in the art, the specific meaning of the above terms in the present invention may be understood in specific circumstances.

In the description of the present invention, it should be noted that, in the case of no conflict, the embodiments in the present disclosure and the characteristics in the embodiments can be combined.

Figure 2:
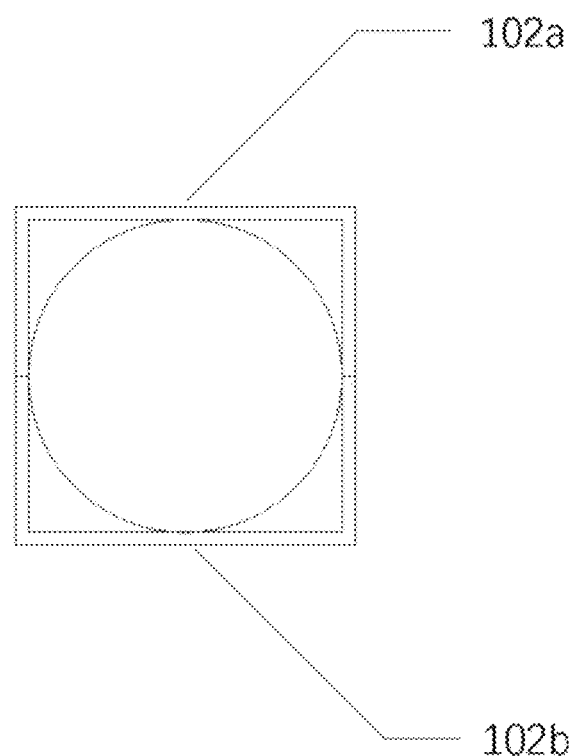
FIG. 2 is a schematic diagram of the stent delivery component in FIG. 1 at a second viewing angle.

Referring to FIG. 1 and FIG. 2, FIG. 1 is a structural schematic diagram of a stent delivery component at a first viewing angle according to a first embodiment of the present disclosure. FIG. 2 is a structural schematic diagram of the stent delivery component in FIG. 1 at a second viewing angle. As shown in FIG. 1, the stent delivery component 1 in the present embodiment includes a base 101 and clamping wings 102. The clamping wings 102 further include a first clamping wing 102a and a second clamping wing 102b.

In the present embodiment, the first clamping wing 102a and the second clamping wing 102b are rotatably connected respectively with the base 101. It can be easily understood by those skilled in the art that the above rotatable connection may refer to any connection mode that can make two connected components rotate relatively, such as hinge connection, bearing connection, pin shaft connection, flexible bending connection, etc.

In the present embodiment, the first clamping wing 102a and the second clamping wing 102b can jointly form an enclosing section of a prismatic shape in a first position state. The first position state may be a state in which the adjacent clamping wings are in direct contact or at a small spacing. For example, in FIG. 2, the first clamping wing 102a and the second clamping wing 102b contact each other.

In the present embodiment, the enclosing section may be a structure with a generally prismatic shape. In an example, the shape of the enclosing section may be a regular prism, such as a regular triangular prism, a regular quadrangular prism, a regular pentagonal prism, a regular hexagonal prism, and the like. In FIG. 2, the enclosing section formed by the first clamping wing 102a and the second clamping wing 102b has a regular quadrangular prism shape. It can be easily understood that the regular prism may be regarded as being formed by stretching a regular polygon (such as an equilateral triangle, a square, a regular pentagon, etc.) along a normal line direction.

In the present embodiment, the enclosing section may have an internal space for enclosing at least part of the stent. In an example, the internal space can accommodate the whole stent. In another example, the internal space can accommodate a portion of the stent. Other portions of the stent pass through an opening of the internal space and are kept outside.

In the present embodiment, the internal space of the enclosing section may be closed, and may also have an opening on at least one portion. For example, the enclosing section shown in FIG. 2 has a square opening (i.e., the square at the inner side in FIG. 2). Furthermore, if end surfaces of the contacted clamping wings in FIG. 2 are cut off, an opening of the enclosing section extending in a direction perpendicular to the paper surface may be formed.

In the present embodiment, the internal space of the enclosing section may be cylindrical, prismatic, etc.

In the present embodiment, the first clamping wing 102a and the second clamping wing 102b move away from each other when rotated from the first position state to the second position state, so that the enclosing section of the stent delivery component 1 is expanded, and the enclosing effect or limiting effect of the enclosing section on the stent is reduced, thereby making the stent that is at least partially accommodated therein released. The second position state, for example, is the position state of the first clamping wing 102a and the second clamping wing 102b shown in FIG. 1, i.e., the state in which the distal ends of the clamping wings are widely spaced.

In the present embodiment, at least two clamping wings jointly form the enclosing section of the prismatic shape when located in the first position state, and the enclosing section has the internal space for enclosing at least part of the stent, so that on one hand, the stent can be enclosed effectively so as to complete delivery; and on the other hand, the stent delivery component is kept in line contact with an inner wall of the delivery catheter, so that the contact area is reduced, thereby reducing the frictional resistance, reducing the operation difficulty and increasing the delivery efficiency.

In an example, as shown in FIG. 1, the first clamping wing 102a and the second clamping wing 102b both are concave plate structures. The concave plate structure may be regarded as being obtained by bending two lengthwise edges of a flat plate towards the same side, and may also be regarded as being obtained by cutting a thin-walled tube in a shape of regular quadrangular prism along a symmetric surface parallel to one side surface. The clamping wings are designed to be the concave plate structures, so that the structural complexity and manufacturing difficulty of the stent delivery component 1 can be reduced.

In the above example, the first clamping wing 102a and the second clamping wing 102b of the concave plate structure are spliced into the enclosing section of a regular quadrangular prism shape in the first position state. FIG. 2 is observed from an open end of the cavity of the stent delivery component along the central line of the regular quadrangular prism. The square at the outer side in FIG. 2 corresponds to the bottom surface of the regular quadrangular prism of the enclosing section. By adopting the regular quadrangular prism form, the number of line contacts (four line contacts) between the stent delivery component 1 and the inner wall of the delivery catheter 4 can be reduced, thereby further reducing the frictional resistance in the delivery process.

In the above example, as shown in FIG. 2, the internal space of the enclosing section is also in a shape of regular quadrangular prism. The bottom surface of the internal space corresponds to the square atvthe inner side in FIG. 2. The shape of the internal space corresponds to the regular quadrangular prism shape of the enclosing section and can be regarded as being obtained by zooming out the shape of the regular quadrangular prism according to a specific ratio. In this circumstance, the enclosing section may be regarded as the thin-walled tube of regular quadrangular prism. The internal space is designed to be the shape corresponding to the shape of regular quadrangular prism, thereby increasing the size of the internal space, so that the overall size of the stent delivery component is reduced.

In an example, the stent delivery component 1 may be made of a polymer material, which may adopt, for example, a nylon material, a PTEE (Polytetra fluoro ethylene) material, a Pebax (block copolymers of polyamide and polyether) material, a TPU (thermoplastic urethane) material, a PET (polyethylene terephthalate) material, a PE (polyethylene) material, a PVC (polyvinyl chloride) material, a PC (polycarbonate) material, a POM (polyformaldehyde) material, an organic silicon resin material, a PU (polyurethane) material, an ABS (acrylonitrile butadiene styrene) material, a PEEK (Poly-ether-ether-ketone) material, a PU (polyurethane) material, etc. By adopting the polymer material, the weight of the stent delivery component is reduced, the manufacturing cost is reduced, etc. In other examples, the stent delivery component 1 may also be made of a metal material, for example, titanium, nickel-titanium alloy, stainless steel, platinum-tungsten alloy, platinum, platinum-iridium alloy, cobalt-chromium alloy, etc. The base 101 and the clamping wings 102 may be made of the same material or different materials.

In an example, as shown in FIG. 1, the base 101 is a tubular structure, for example, a round tube structure. In this way, the base and the stent delivery component can be manufactured conveniently, and it is conducive to sleeving the base 101 with the delivery guide wire 3. In other examples, the base 101 may also be a non-tubular structure, such as solid cylinder, solid prism, etc.

In an example, as shown in FIG. 1, the stent delivery component 1 is manufactured integrally. The rotatable connection between the clamping wings and the base is implemented on the basis of the flexible bending between the clamping wings and the base. For example, flexible plastics can be injection molded into the round tube structure first, and then one portion of the round tubule structure is fixed on a forming mold of the quadrangular prism shape. Then the portion becomes the thin-walled tube of the regular quadrangular prism shape through a heating forming method, and the natural transition between the quadrangular prism structure and the round tube structure is realized. Finally, the thin-walled tube of the regular quadrangular prism shape is sectioned along the symmetric surface parallel to one side surface to form the two clamping wings, and each clamping wing is bent from the root of a cut mark. Since the stent delivery component 1 is made of a flexible material, the clamping wings and the base are kept in connection at a fold, and can also rotate relative to each other. By manufacturing the stent delivery component integrally and adopting the flexible bending way, the stent delivery component can be manufactured simply and efficiently.

In an example, a length L of the clamping wing satisfies the formula (1):

$$L \geq \left| \frac{D}{2\sin\theta} \right| \quad \text{Formula (1)}$$

In the formula (1), D represents an outer diameter of the stent, and θ represents a rotating angle of the clamping wing relative to the first position state, $0° < \theta \leq 90°$. The lower limit of the length L of the clamping wing here can ensure that the enclosed portion of the stent is expanded slowly in the release process. If the clamping wing is excessively short, the enclosed portion of the stent may be popped up rapidly in the release process, which may injure the blood vessel.

Furthermore, generally when in clinical use by doctors, the diameter of the stent is greater than that of the blood vessel; therefore, it can be seen from the formula (1) that twice the length (i.e., 2L) of the clamping wing is greater than the diameter of the blood vessel. In an example wherein two clamping wings are included, when the two clamping wings are opened in the blood vessel, and because the diameter of the blood vessel is less than 2L, an unfolding angle of the two clamping wings may be less than 180°. In this regard, the lower limit of the length L of the clamping wing can also prevent the angle between the two clamping wings being greater than 180° after complete release of the stent, so that the problems that the stent delivery component injures the blood vessel, or the stent delivery component cannot be retrieved into the delivery catheter can be avoided.

In an example, the length L of the clamping wing also satisfies the formula (2):

$$L \leq 0.7 L_0 \quad \text{Formula (2)}$$

In the formula (2), $L_0$ represents the length of the stent. The upper limit of the length L of the clamping wing here can prevent the clamping wing from being too long to affect the separation between the stent delivery component and the stent, thereby guaranteeing the success in releasing the stent.

Figure 3:
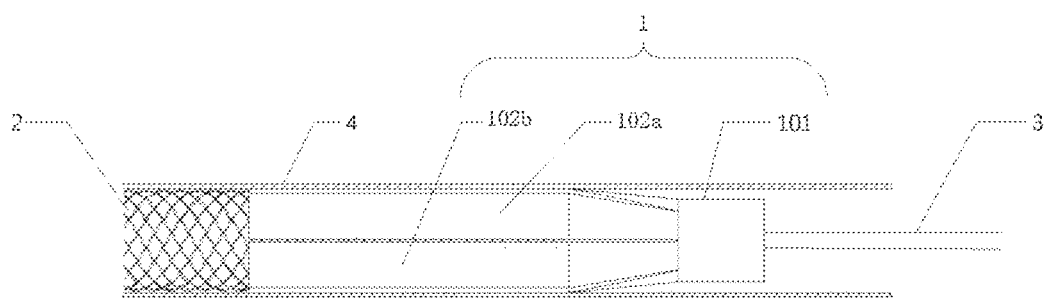
FIG. 3 is a schematic diagram of a stent system in a compressed state at a first viewing angle according to an embodiment of the present disclosure.
Figure 4:
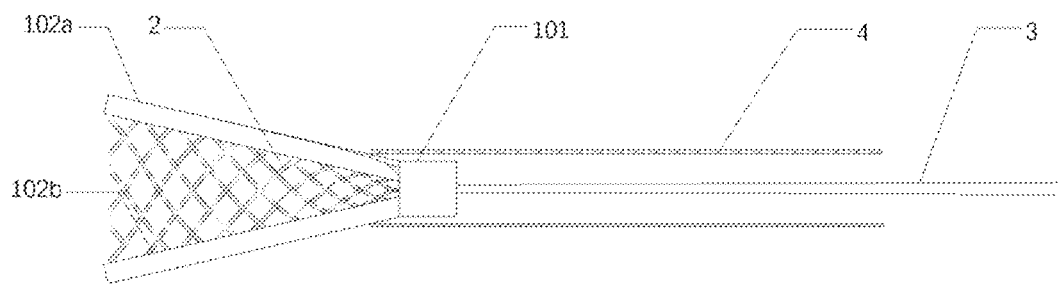
FIG. 4 is a schematic diagram of the stent system in a partially release state according to an embodiment of the present disclosure.
Figure 5:
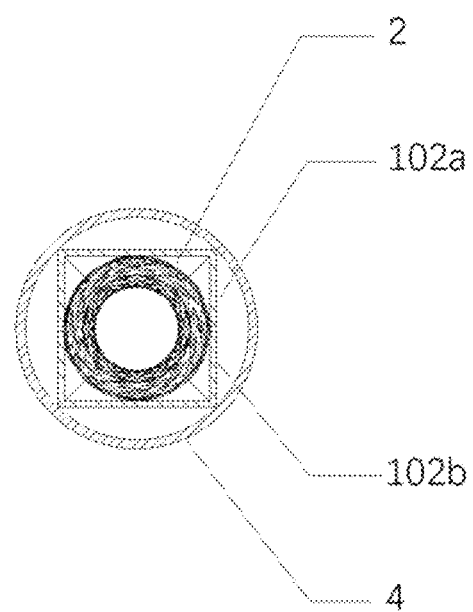
FIG. 5 is a schematic diagram of the stent system in FIG. 3 at a second viewing angle.

With reference to FIGS. 3 to 5, how to convey the stent by using the stent delivery component in the present embodiment is described below. FIG. 3 is a schematic diagram of a stent system in a compressed state at a first viewing angle according to the present embodiment. FIG. 4 is a schematic diagram of the stent system in a partial release state according to the present embodiment. FIG. 5 is a schematic diagram of the stent system in FIG. 3 at a second viewing angle.

As shown in FIG. 3, the stent system includes a stent 2, delivery catheters 4, delivery guide wires 3 and a stent delivery component 1. A base 101 of the stent delivery component 1 is connected fixedly with distal ends of the delivery guide wires 3. Generally speaking, the end operated by an operator such as the doctor is referred to as a proximal end, and the end inserted into the human body is referred to as a distal end. The above fixed connection may be implemented by binding, welding, integrally manufacturing and other methods. The stent 2 is at least partially accommodated in an internal space of the stent delivery component 1. At least part of the delivery guide wire 3, the stent delivery component 1 and the stent 2 are accommodated in the delivery catheter 4, and the stent 2 is in a compressed state.

In the delivery process of the stent, the delivery catheter 4 may be sent into the human body first, and the opening on the distal end of the delivery catheter is located nearby a target position. Then the delivery guide wires 3 are pushed to convey the stent delivery component 1 connected therewith towards the distal end. The stent 2 is driven by the stent delivery component 1 to move together.

As shown in FIG. 4, after the stent 2 reaches the opening on the distal ends of the delivery catheters 4, the delivery guide wires 3 are pushed continuously to gradually move the stent 2 out of the catheters. Since the stent 2 has elasticity, the portion moved out of the catheters may be unfolded along the radial direction under the effect of the elasticity, and each clamping wing of the stent delivery component 1 is driven to rotate in a direction away from the central line of the delivery catheter, so that the enclosing section of the stent delivery component 1 is expanded, and the internal space is opened.

In the release process of the stent, if the stent needs to be retrieved due to factors such as wrong release position, the operation personnel can pull the delivery guide wires 3 along the proximal end direction. At this time, the stent delivery component 1 may move towards the proximal end direction along with the delivery guide wires 3. Due to the limitation of the opening of the delivery catheters 4, each clamping wing of the stent delivery component 1 may rotate towards the central line of the delivery catheter, thereby compressing the stent 2 to make it retrieved successfully. After the stent delivery component 1 completely enters the delivery catheters 4, an inner cavity of the stent delivery component 1 is formed again to accommodate the stent 2.

As shown in FIG. 3, in the delivery process of the stent, since the stent 2 is at least partially accommodated in the internal space of the stent delivery component 1, this portion is not in direct contact with the delivery catheter 4, and the stent delivery component 1 directly contacts the delivery catheter 4. Therefore, the frictional force between the stent delivery component 1 and the inner wall of the delivery catheter 4 have great impact on the delivery resistance. In the stent delivery component provided by the present embodiment, at least two clamping wings are spliced into an enclosing section of a prismatic shape in a first position state, so that the stent delivery component is kept in line contact with the inner wall of the delivery catheter, and the contact area is reduced, thereby reducing the frictional resistance, reducing the operation difficulty and increasing the delivery efficiency.

Figure 6:
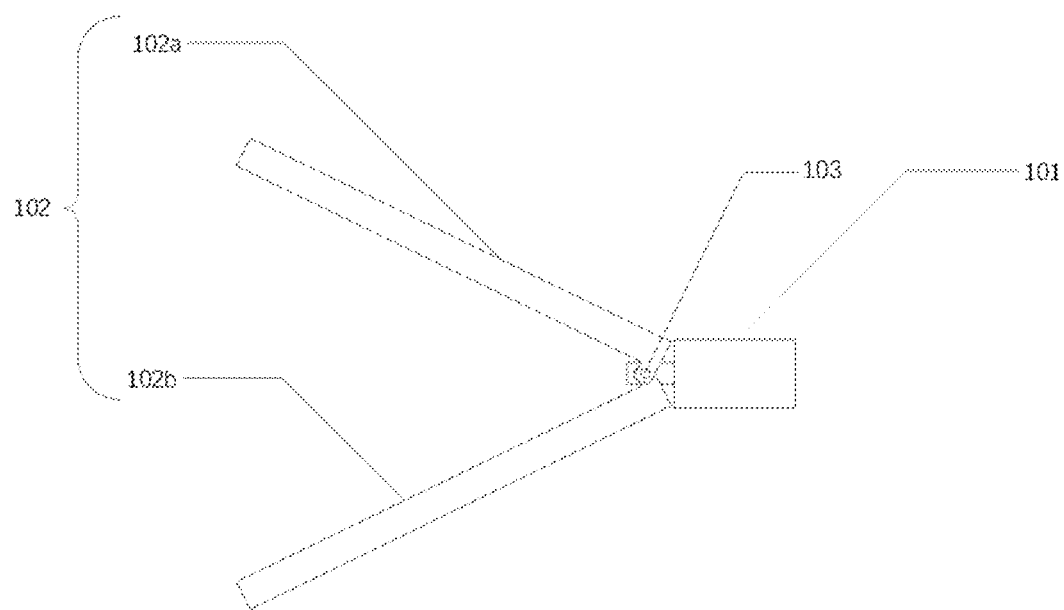
FIG. 6 is a structural schematic diagram of the stent delivery component at a viewing angle according to a second embodiment of the present disclosure.

Referring to FIG. 6, FIG. 6 is a structural schematic diagram of the stent delivery component at a viewing angle according to a second embodiment of the present disclosure. The present embodiment differs from the first embodiment in that: as shown in FIG. 6, the rotatable connection between the clamping wings and the base 101 is implemented through a pin shaft 103. Furthermore, each clamping wing and the base in the present embodiment are not manufactured integrally, but are assembled after being manufactured separately. For example, the base 101, the first clamping wing 102*a* and the second clamping wing 102*b* are manufactured separately by metal materials first, and then the clamping wings are hinged with the base through the pin shaft 103.

Other details and technical effects of the stent delivery component in the present embodiment can refer to the description in the first embodiment and are not repeated here.

Figure 7:
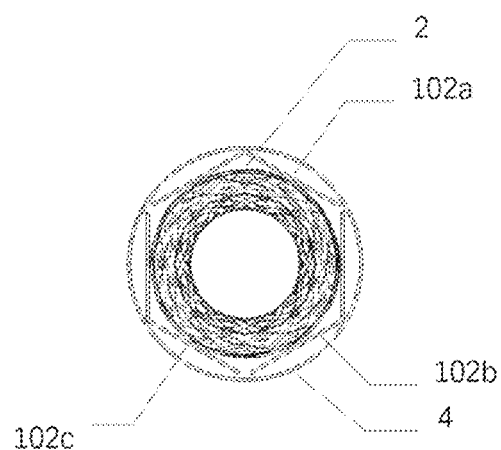
FIG. 7 is a structural schematic diagram of the stent delivery component at a viewing angle according to a third embodiment of the present disclosure.

Referring to FIG. 7, FIG. 7 is a structural schematic diagram of the stent delivery component at a viewing angle according to a third embodiment of the present disclosure. Comparing FIG. 7 with FIG. 5, different from the stent delivery component in the first embodiment that includes two clamping wings, the stent delivery component in the present embodiment includes a first clamping wing 102*a*, a second clamping wing 102*b* and a third clamping wing 102*c*. Furthermore, the enclosing section formed by each clamping wing in the present embodiment in the first position state has a shape of regular hexagonal prism.

More clamping wings of the stent delivery component in the present embodiment are conducive to reducing the weight of each clamping wing, so that the stent is released more successfully. Furthermore, the more the sides of the shape of the enclosing section in the present embodiment, the greater the bottom area, which is conducive to increasing the size of the internal space, so that the overall size of the stent delivery component is reduced.

It can be easily understood by those skilled in the art that other numbers of clamping wings and/or the prismatic shape with other number of sides can be used.

Figure 8:
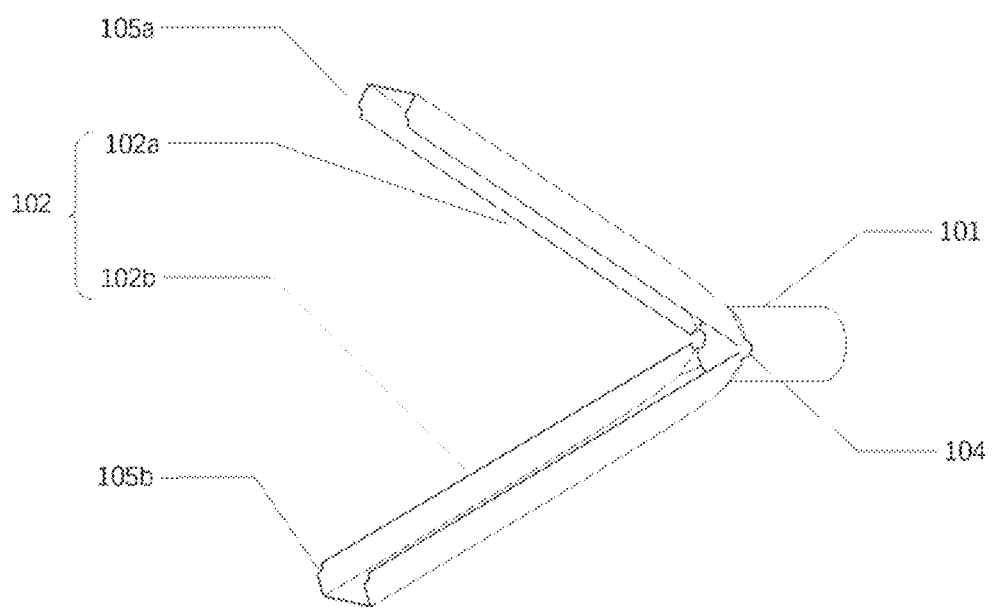
FIG. 8 is a structural schematic diagram of the stent delivery component at a viewing angle according to a fourth embodiment of the present disclosure.

Referring to FIG. 8, FIG. 8 is a structural schematic diagram of the stent delivery component at a viewing angle according to a fourth embodiment of the present disclosure. In the present embodiment, a first hollowing structure 104 is arranged at a junction between two adjacent clamping wings 102*a* and 102*b* and the base 101.

In the present embodiment, the first hollowing structure 104 is a circular hole. In other embodiments, the first hollowing structure may also be square or other shapes.

In the present embodiment, the first hollowing structures 104 are arranged respectively at two sides of the stent delivery component. In other embodiments, the first hollowing structure may also be a through hole extending from one side of the stent delivery component to the other side.

In the present embodiment, the first hollowing structure 104 is formed jointly by a quarter circular notch located at the first clamping wing 102*a*, a quarter circular notch located at the second clamping wing 102*b* and a semicircular notch located on the base 101. When the two clamping wings 102*a* and 102*b* are located in the first position state, the first hollowing structure 104 is a closed circular hole. When the two clamping wings 102*a* and 102*b* are located in the second position state, the first hollowing structure 104 is a non-closed state.

In the present embodiment, by arranging the first hollowing structure, sharp corners on rotatable connection ends can be prevented from colliding with each other when the clamping wings are closed and from hindering the closing of the clamping wings.

In the present embodiment, a second hollowing structure is arranged at an adjoint of the distal ends of the two adjacent clamping wings 102*a* and 102*b*. It can be easily understood that the above "adjoint" may refer to that the distal ends of the two adjacent clamping wings are close to each other or are in direct contact. The second hollowing structure includes a first portion 105*a* and a second portion 105*b*. The first portion 105*a* and the second portion 105*b* both are quarter circular notches.

In the present embodiment, the second hollowing structure is fan-shaped (semicircular). In other embodiments, the second hollowing structure may also be arc or square, etc.

In the present embodiment, by arranging the second hollowing structure, sharp corners on rotatable connection ends can be prevented from colliding with each other when the clamping wings are closed and from hindering the closing of the clamping wings.

A fifth embodiment of the present disclosure provides a stent system. The stent system, as shown in FIG. 4, includes delivery catheters 4, a stent 2, delivery guide wires 3 and a stent delivery component 1. A base 101 of the stent delivery component 1 is connected fixedly with distal ends of the delivery guide wires 3. The stent 2 is at least partially accommodated in an internal space of the stent delivery component 1. At least part of the delivery guide wire 3, the stent delivery component 1 and the stent 2 are accommodated in the delivery catheters 4, and are in a compressed state. The stent 2 may be, but not limited to, a self-expanding stent or a self-swelling stent.

Specific details and technical effects of the stent system in the present embodiment can refer to relevant description in the first embodiment and are not repeated here.

Figure 9:
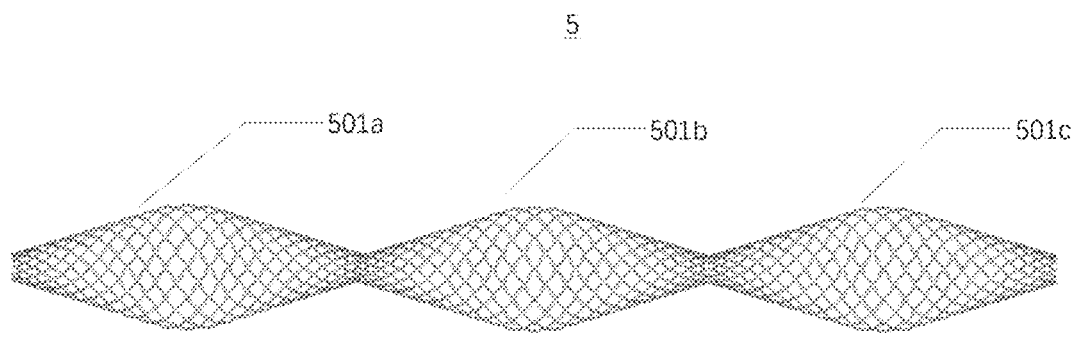
FIG. 9 is a structural schematic diagram of a beaded component at a viewing angle according to a fifth embodiment of the present disclosure.

In an example, the stent system may also include a beaded component. FIG. 9 is a structural schematic diagram of a beaded component at a viewing angle. As shown in FIG. 9, the beaded component 5 includes a first expanding section 501*a*, a second expanding section 501*b* and a third expanding section 501*c*.

In this example, the beaded component 5 may also be formed by a metal wire or a coil. Each expanding section may be spindle, and has elasticity. The expanding sections can be compressed and restored to an original shape under the action of elasticity.

In this example, in the stent system, the proximal end of the beaded component 5 is connected fixedly with the distal ends of the delivery guide wires 3 or the base of the stent delivery component 1. The beaded component 5 is at least partially accommodated in the stent. The beaded component 5 may be designed as being disposed inside the stent and contracted along with the stent so as to be accommodated in the delivery catheters. After reaching a target part, the beaded component 5 and the stent can be pushed out together by pushing the delivery guide wires from the distal ends. The stent is unfolded after the expanding sections of the beaded component 5 are expanded, so that the stent is released more sufficiently on the target part.

In an example, the stent 2 is a cardiovascular self-expanding stent, a peripheral self-expanding stent or a cerebrovascular self-expanding stent. The cardiovascular self-expanding stent can be used in heart blood vessels. The peripheral self-expanding stent can be used in peripheral blood vessels. The cerebrovascular self-expanding stent can be used in cerebral vessels.

Specific details and technical effects of the stent delivery system in the present embodiment can refer to relevant description in the first embodiment and fourth embodiment, and are not repeated here.

The above descriptions are preferred embodiments of the present disclosure and description of the applied technical principles. It should be understood by those skilled in the art that the scope of the invention involved in the present disclosure is not limited to the technical solution formed by the specific combination of the above technical features, but also covers other technical solutions formed by any combination of the above technical features or their equivalent features without departing from the above inventive concept, such as The technical solution formed by replacing the above features with the technical features with similar functions disclosed (but not limited to) in the present disclosure.

The invention claimed is:

1. A stent delivery component for delivering a stent, comprising a base, a beaded component, at least two clamping wings, and a delivery guide wire,
    wherein the at least two clamping wings are rotatably connected with the base, respectively;
    wherein the at least two clamping wings jointly form an enclosing section of a prismatic shape when being in a first position state, and the enclosing section has an internal space for enclosing at least part of the stent when the stent is in a compressed state;
    wherein the at least two clamping wings are separated from each other to make the enclosing section expanded when rotated from the first position state to a second position state; and
    wherein length L of each clamping wing satisfies:

$L \leq 0.7 L_0$ wherein $L_0$ represents the length of the stent;
    wherein the stent is elastic;
    wherein the beaded component comprises at least one expanding section and is configured to expand to unfold and release the stent;
    wherein a proximal end of the beaded component is connected fixedly with the base of the stent delivery component and the distal end of the delivery guide wire; and
    wherein the distal end of the beaded component is distal to the delivery guide wire and the base of the stent delivery component.

2. The stent delivery component of claim 1, wherein the rotatable connection is any one or a combination of hinge connection, bearing connection, pin shaft connection and flexible bending connection.

3. The stent delivery component of claim 1, wherein the enclosing section has a regular prism shape.

4. The stent delivery component of claim 3,
    wherein the enclosing section has the regular quadrangular prism shape; and
    wherein the number of the clamping wings is two.

5. The stent delivery component of claim 1, wherein the stent delivery component comprises a polymer material and/or metal material.

6. The stent delivery component of claim 5, wherein the polymer material is selected from a nylon material, a PTFE material, a Pebax material, a TPU material, a PET material, a PE material, a PVC material, a PC material, a POM material, an organic silicon resin material, an ABS material, a PEEK material and a PU material; and
    wherein the metal material is selected from titanium, nickel-titanium alloy, stainless steel, platinum-tungsten alloy, platinum, platinum-iridium alloy and cobalt-chromium alloy.

7. The stent delivery component of claim 1, wherein a first hollowing structure is arranged at the junction between two adjacent clamping wings and the base; optionally, the first hollowing structure is a circular hole or a square hole.

8. The stent delivery component of claim 2, wherein the stent delivery component is manufactured integrally, and the rotatable connection is the flexible bending connection.

9. The stent delivery component of claim 3, wherein the enclosing section has any one of a regular quadrangular prism shape, regular pentagonal prism shape and regular hexagonal prism shape.

10. The stent delivery component of claim 4, wherein the base is a tubular structure.

11. The stent delivery component of claim 3, wherein the stent delivery component comprises a polymer material and/or metal material.

12. The stent delivery component of claim 7, wherein a second hollowing structure is arranged at an adjoint of distal ends of the two adjacent clamping wings; optionally, the second hollowing structure is in a fan shape, an arc shape or a square shape.

13. A stent delivery system for delivering a stent, comprising
    a delivery catheter,
    a delivery guide wire,
    a stent delivery component that comprises a base and at least two clamping wings, wherein the at least two clamping wings are rotatably connected with the base, respectively, and
    a beaded component, wherein the beaded component comprises at least one expanding section and is configured to expand to unfold and release the stent, and wherein a proximal end of the beaded component is connected fixedly with a distal end of the delivery guide wire and the base of the stent delivery component;
    wherein the at least two clamping wings jointly form an enclosing section of a prismatic shape when being in a first position state, and the enclosing section has an internal space for enclosing at least part of the stent when the stent is in a compressed state;
    wherein the at least two clamping wings are separated from each other to make the enclosing section expanded when rotated from the first position state to a second position state; and
    wherein length L of each clamping wing satisfies:

$L \leq 0.7 L_0$ wherein $L_0$ represents the length of the stent;
wherein the stent is elastic;
wherein the base of the stent delivery component is connected fixedly with a distal end of the delivery guide wire;
wherein the distal end of the beaded component is distal to the delivery guide wire and the base of the stent delivery component; and
wherein at least part of the delivery guide wire and the stent delivery component are accommodated in the delivery catheter.

14. The stent delivery system of claim 13, wherein the rotatable connection is any one or a combination of hinge connection, bearing connection, pin shaft connection and flexible bending connection; optionally, the stent delivery component is manufactured integrally, and the rotatable connection is the flexible bending connection.

15. The stent system of claim 13, wherein the beaded component is at least partially accommodated in the stent.

16. The stent system of claim 15, wherein the stent is a cardiovascular self-expanding stent, a periphery self-expanding stent or a cerebrovascular self- expanding stent.

17. The stent delivery system of claim 13, wherein the enclosing section of the stent delivery component has a regular prism shape; optionally, the enclosing section has any one of a regular quadrangular prism shape, regular pentagonal prism shape and regular hexagonal prism shape.

18. The stent delivery system of claim 17, wherein the enclosing section has the regular quadrangular prism shape; and wherein the number of the clamping wings is two.

19. The stent delivery system of claim 13, wherein the stent delivery component comprises a polymer material that is selected from a nylon material, a PTEE material, a Pebax material, a TPU material, a PET material, a PE material, a PVC material, a PC material, a POM material, an organic silicon resin material, an ABS material, a PEEK material and a PU material, and/or a metal material that is selected from titanium, nickel-titanium alloy, stainless steel, platinum-tungsten alloy, platinum, platinum-iridium alloy and cobalt-chromium alloy.

20. The stent delivery system of claim 13, wherein the stent delivery component comprises a first hollowing structure that is arranged at the junction between two adjacent clamping wings and the base; optionally, the first hollowing structure is a circular hole or a square hole; and optionally, wherein the stent delivery component comprises a second hollowing structure is arranged at an adjoint of distal ends of the two adjacent clamping wings; optionally, the second hollowing structure is in a fan shape, an arc shape or a square shape.

21. A stent system comprising the stent and the stent delivery system of claim 13, wherein the stent is at least partially accommodated in the internal space of the stent delivery component; and wherein the stent is accommodated in the delivery catheter.

* * * * *